United States Patent [19]

Miyashita et al.

[11] Patent Number: 4,714,675

[45] Date of Patent: Dec. 22, 1987

[54] STABILIZED SENSITIVITY TEST DISK

[75] Inventors: Yoshinobu Miyashita, Osaka; Tadashi Hamanaka, Kobe; Kenzi Iwata, Osaka, all of Japan

[73] Assignee: Wako Pure Chemical Industries, Ltd., Osaka, Japan

[21] Appl. No.: 504,956

[22] Filed: Jun. 16, 1983

[30] Foreign Application Priority Data

Apr. 13, 1982 [JP] Japan ................... 57-61336

[51] Int. Cl.⁴ .......................... C12Q 1/18; C12Q 1/34
[52] U.S. Cl. ........................................ 435/32; 435/18; 435/805; 422/57
[58] Field of Search ................... 435/32, 33, 805, 871, 435/300, 7, 18, 291, 299; 422/57

[56] References Cited

U.S. PATENT DOCUMENTS

| | | | |
|---|---|---|---|
| 3,216,907 | 11/1965 | Goldman | 435/32 |
| 3,713,985 | 1/1973 | Astle | 435/7 |
| 3,936,355 | 11/1973 | Lawson | 435/871 |
| 3,937,655 | 2/1976 | Pfeiffer et al. | 435/805 |
| 3,992,265 | 11/1976 | Hansen | 435/300 |
| 4,153,512 | 5/1979 | Messner et al. | 435/33 |
| 4,250,256 | 2/1981 | Wielinger et al. | 435/32 |
| 4,381,343 | 4/1983 | Citri | 435/32 |

FOREIGN PATENT DOCUMENTS

| | | | |
|---|---|---|---|
| 0692124 | 8/1964 | Canada | 435/32 |
| 0883389 | 11/1961 | United Kingdom | 435/32 |

OTHER PUBLICATIONS

Merck Index *Eighth edition, pp. 683 and 849.

*Primary Examiner*—Esther M. Kepplinger
*Attorney, Agent, or Firm*—Armstrong, Nikaido, Marmelstein & Kubovcik

[57] ABSTRACT

Stability of a sensitivity test disk obtained by impregnating a disk carrier with an aqueous solution of antibacterial agent and drying is improved by incorporating a water-soluble polymer material having film-forming properties in the disk carrier.

8 Claims, No Drawings

STABILIZED SENSITIVITY TEST DISK

This invention relates to a sensitivity test disk of microorganisms to antibacterial agents such as synthetic chemotherapeutic agents, antibiotics, etc., obtained by impregnating a disk carrier such as paper, nonwoven fabric, etc., with an antibacterial agent, characterized by containing a water-soluble polymer material in the disk carrier as stabilizer.

Recent progress of chemotherapy to bacteria infectious diseases is remarkable and new antibacterial substances are developed one after another. On the other hand, it is indispensable for practicing suitable chemotherapy to select the most suitable antibacterial agent against a causing bacterium of bacterial infectious disease. An antibiotic sensitivity test (or a susceptibility test) is an extremely important clinical test for giving basic data for selecting drugs and determining dosage or dosing method. Therefore, the antibiotic sensitivity test requires reproducibility and reliability of test results.

In the antibiotic sensitivity test, there is widely used a sensitivity disk method wherein a disk carrier such as filter paper, or the like is impregnated with an antibacterial agent solution and dried. But, there are the following major factors which influence the sensitivity test results:

(1) Antibacterial agent content in a disk and scattering of the content.

(2) Measuring conditions (medium used, inoculated amount of bacterium, culture conditions).

(3) Judging method.

Thus, it is important to supply stable sensitivity disks.

Among antibacterial agents, some are relatively low in stability. Particularly when they are impregnated in disks such as filter paper with a low concentration, the antibacterial agent content is often lowered during the production of disk or the storage of filter paper impregnated with the antibacterial agent. Most antibiotics are in general relatively stable in the form of pharmaceutical preparation, but some are unstable. Even if a relatively stable antibiotic is impregnated in a disk such as filter paper for the sensitivity test in lower concentration, it sometimes becomes unstabilized and difficult to maintain a constant potency of antibiotics for a certain period. In the case of unstable antibiotics, stability of sensitivity test disks impregnated with such unstable antibiotics cannot be expected.

Further, the potency of some antibacterial agents is lowered by temperature, moisture absorption, etc. In order to prevent moisture absorption, it is necessary to store sensitivity test disks together with a hygroscopic silicon compound, and there is a fear of damaging the reliability of test results unless these test disks are used in a short period once exposed to an outer atmosphere, since there is always a danger of moisture absorption.

In the production of the sensitivity test disk, a carrier such as filter paper is impregnated with an antibacterial agent solution and dried so as to make the antibacterial agent adsorbed uniformly on the surface of the carrier. But such a sensitivity disk seems to be influenced easily by outside conditions such as those resulting in moisture absorption, since the surface area of the disk carrier is placed in a position to widely contact with the outer atmosphere with ease.

On the other hand, when the sensitivity disk is placed on an agar culture medium coated with a test strain for test, it is necessary that the anti-bacterial agent impregnated therein should disperse uniformly around the sensitivity disk.

The present inventors have studied the abovementioned problems extensively and found that when an impregnating solution wherein an antibiotic was dissolved mixed with a water-soluble polymer material, stability after the production of disk was improved remarkably and the water-soluble polymer material had no bad influence on the dispersion of the antibiotic contained in the disk at the time of sensitivity test, and have accomplished this invention.

This invention provides a sensitivity test disk of microorganisms to antibacterial agents containing an antibacterial agent uniformly dispersed in a disk carrier, characterized by containing a water-soluble polymer material having film-forming properties as a stabilizer in the disk carrier.

When a water-soluble polymer material is added to an impregnating solution wherein an antibacterial agent is dissolved, which solution is to be used for impregnating the disk carrier such as filter paper and dried, the antibacterial agent covered with the water-soluble polymer material can be adsorbed on the surface of the carrier material. Such a structure is effective for protecting the antibacterial agent from influences of the outer atmosphere such as those resulting in moisture absorption.

Cephem antibiotics can be represented by the following formula:

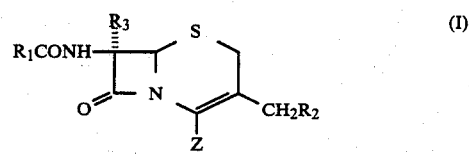

wherein $R_1$ and $R_2$ are groups which can show antibiotic properties; $R_3$ is hydrogen or methoxy; Z is COO− or COOX in which X is hydrogen, an alkali metal, an alkaline earth metal or an ester group which is easily hydrolyzable or metabolizable and is pharmaceutically acceptable.

The bonding between —$CH_2$ and $R_2$ in the cephem antibiotics easily brings about hydrolysis in the presence of moisture and even in the form of crystal the cephem antibiotics suffer hydrolysis during storage for a long period of time when water is contained therein and deterioration takes place.{J. Takeda Res. Lab., 37 (3/4), 286–296 (1978) (Published by Takeda Chemical Industries, Ltd.)}

On the other hand, penicillin antibiotics can be represented by the following formula:

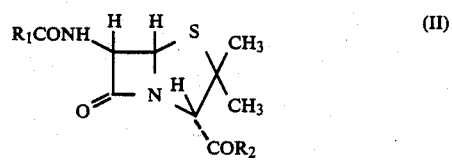

wherein $R_1$ and $R_2$ are groups which can show antibiotic properties. The penicillin antibiotics are relatively stable in the form of powder but unstable in the form of aqueous solution. This seems to be caused by hydrolysis of the acid amide group as shown in the above structural formula. (Handbook of Antibiotics, published by Sangyo Tosho Co., Ltd. page 112 (1969)).

As mentioned above, in such antibiotics as cephem and penicillin antibiotics, a main decomposition reaction is hydrolysis caused by moisture absorption. Therefore, the most important stabilizing method of these antibiotics contained in sensitivity disks is to prevent moisture absorption.

As to the water-soluble polymer material having film-forming properties, it is important that said polymer material is impregnated in the disk carrier as an aqueous solution containing an antibiotic and once dried, results in a dried body which hardly absorb moisture from the ambient atmosphere. For example, in the case of poly(vinyl alcohol), when filter paper is impregnated with an aqueous solution of poly(vinyl alcohol) and dried in a high degree, lowering in water absorption is observed and sometimes water repellency is observed. Therefore, as the water-soluble polymer material, there is selected one showing resistance to moisture absorption when it is impregnated in the disk carrier as an aqueous solution containing an antibiotic which is subsequently dried.

The stabilizing mechanism of the water-soluble polymer material when applied to an antibacterial agent such as antibiotic is not clear, but the antibacterial agent seems to be covered with the water-soluble polymer material and is thereby protected from moisture in the outer atmosphere.

On the other hand, since the polymer material used has water-soluble properties, the resulting dried sensitivity disk can easily be swollen by the moisture in an agar culture medium at the time of the antibiotic sensitivity test and there is no effect on the dispersion of the antibacterial agent into the culture medium.

The prevention of moisture absorption by the use of water-soluble polymer material and the use of water-soluble polymer material having no effect on the dispersion of the antibacterial agent in the sensitivity test cannot be expected from the prior art.

It is important that the polymer material used in this invention has solubility in water and also has film-forming properties upon drying. Examples of such a polymer material are poly(vinyl alcohol) and cellulose derivatives.

As the poly(vinyl alcohol), those having a degree of polymerization of 500 to 2000 are suitable.

As the cellulose derivatives, there can be used methyl cellulose, hydroxypropylmethyl cellulose, hydroxypropylethyl cellulose, hydroxypropyl cellulose, hydroxyethyl cellulose, and the like.

The water-soluble polymer material is used in a concentration of 0.1 to 1.0% by weight based on the weight of an aqueous solution containing an antibacterial agent and the water-soluble polymer material. The concentration of 0.4 to 0.6% by weight is more preferable. If the amount of the water-soluble polymer material is too small, the effect of using such a material cannot be obtained, whereas if the amount is too high, the releasing rate of the antibacterial agent becomes too slow at the time of sensitivity test.

Some antibacterial agents have a pH range in which the hydrolysis reaction rate is small and stability is high. For example, cephem antibiotics show good stability at a pH of 4 to 5 and penicillin antibiotics show good stability at a pH of 6 to 6.5. In such a case, in order to maintain such a pH range, it is possible to add a buffer solution such as a phosphate buffer, citrate buffer or the like to the impregnating solution without adversely affecting the antibiotic sensitivity test.

When the water-soluble polymer material is used in a pH range wherein the antibacterial agent shows good stability, the effect of using the polymer material can be enhanced remarkably.

As the disk carrier for impregnating the antibacterial agent, there can be used paper, cloth, nonwoven fabric, etc., and filter paper having a thickness of 0.5 to 1.0 mm is suitably used usually. The form of final test disks is usually a circle, but sometimes may be a square depending on the test methods employed.

Preparation of sensitivity test disks can be carried out either by impregnating disk carriers in an aqueous impregnating solution containing a water-soluble polymer material and an antibacterial agent or by dropping a predetermined amount of an aqueous solution containing a water-soluble polymer material and an antibacterial agent from a micropipette on disk carriers having a certain diameter, for example 6 mm in diameter or in some cases on squares having a side of about 5 mm, followed by drying. The drying can be carried out by a conventional process such as a hot air-blowing drying, drying under a reduced pressure, etc. Alternatively, the sensitivity test disks can be produced by impregnating disk carriers with an aqueous solution containing an antibacterial agent and drying (or without drying), followed by impregnation with an aqueous solution containing a water-soluble polymer material and drying.

Examples of the antibacterial agents which show excellent stabilizing effect according to this invention are cephem antibiotics such as shown by the formula (I) mentioned above, and more concretely cefotiam hydrochloride, cefsulodin sodium, cefaloridine, cefmenoxime, cefmenoxime hydrochloride, cefalotin sodium, cefalexin, ceftazidime, cefoxadinum, cephradine, cefroxime, cefoxitin, cefotaxime, cefazorin, cefapirin, cefatrizine, cefaloglycin, ceftriaxone, cefamandole, cefacetrile, cefoperazone, cefadroxil, cefaclor, latamoxef, cefmetazole and pharmaceutically acceptable salts thereof, etc., and penicillin antibiotics such as shown by the formula (II) mentioned above, and more concretely dimethoxyphenylpenicillin, benzylpenicillin, ampicillin, mecillinam (a metabolic product of pivmecillinam hydrochloride), benzylpenicillin benzathine, benzylpenicillin procaine, benzylpenicillin sodium, benzylpenicillin potassium, benzylpenicillin aminomethomidine, ampicillin ethoxycarbonyloxyethyl, ampicillin sodium, ampicillin phthalidyl, carbenicillin, sulbenicillin, ticarcillin, mezlocillin, apalcillin, piperacillin, axoxicillin, cyclacillin, hetacillin, pivampicillin, bacampicillin, azlocillin, phenoxymethyl penicillin, oxacillin, cloxacillin, dicloxacillin, tranpicillin, pivmecillinam, metampicillin, and phermaceutically acceptable salts thereof.

The stabilizing effect of the water-soluble polymer materials against antibacterial agents (retention percents after being stored at 40° C. for 15 days using a desiccant) are shown in Table 1.

TABLE 1

| Impregnating solvent | Stability of antibiotics | | |
| --- | --- | --- | --- |
| | Cefotiam hydrochloride | Cefsulodin sodium | Benzylpenicillin potassium |
| Water | 78 | 70 | 93 |
| Solvent containing no water-soluble polymer material | 80 | 84 | 95 (at pH 6.5) |
| Solvent containing poly- | 100 | 100 | 100 (at pH 6.5) |

TABLE 1-continued

| Impregnating solvent | Stability of antibiotics | | |
|---|---|---|---|
| | Cefotiam hydrochloride | Cefsulodin sodium | Benzylpenicillin potassium |
| (vinyl alcohol) (degree of polymerization about 2000) | | | |
| Solvent containing poly(vinyl alcohol) (degree of polymerization about 500) | 100 | 100 | 100 (at pH 6.5) |
| Solvent containing hydroxypropylmethyl cellulose | 97 | 99 | 100 (at pH 6.5) |

In Table 1, the same solvent was used as in Example 1 mentioned below, i.e. 100 ml of a 0.1 M citrate buffer solution having a pH of 4.0 containing 0.5 g of a water-soluble polymer material and 150 mg of antibiotic except that the pH in the benzylpenicillin potassium column was changed to 6.5. Sensitivity disks were produced by impregnating disks (filter paper) having a diameter of about 6 mm in an impregnating solvent as listed in Table 1 and dried.

The water-soluble polymer material used in this invention does not show pseudo-positivity or show inhibiting activity against tested strains.

As to the pseudo-positivity, sensitivity tests were conducted by using disks impregnated only with poly(vinyl alcohol) having a degree of polymerization of 500 or 2000 or hydroxypropylmethyl cellulose and containing no antibacterial agent against strains selected from pseudomonos genus, Serratia genus, Staphylococcus genus, and Bacillus genus. As shown in Table 2, no inhibition circle (or zone) was formed around the strains or disks tested in the sensitivity test and the pseudo-positivity was not observed.

TABLE 2

| Strain | Carrier | | |
|---|---|---|---|
| | Carrier containing poly(vinyl alcohol) (degree of polymn. 2000) | Carrier containing hydroxypropylmethyl cellulose | Carrier only |
| Pseudomonas aeruginosa IFO 3919 | Inhibition zone was not formed. | Inhibition zone was not formed. | Inhibition zone was not formed. |
| Bacillus subtilis ATTC 6633 | Inhibition zone was not formed. | Inhibition zone was not formed. | Inhibition zone was not formed. |
| Serratia marcescens IFO 3736 | Inhibition zone was not formed. | Inhibition zone was not formed. | Inhibition zone was not formed. |
| Serratia marcescens IFO 3759 | Inhibition zone was not formed. | Inhibition zone was not formed. | Inhibition zone was not formed. |
| Staphylococcus aureus IFO 3183 | Inhibition zone was not formed. | Inhibition zone was not formed. | Inhibition zone was not formed. |

When the size of inhibition zones (in diameter with a unit of mm in Table 3) was measured in the sensitivity tests using the same strains as listed in Table 2 and cefotiam hydrochloride or cefsulodin sodium as cephem antibiotic with or without poly(vinyl alcohol) having a degree of polymerization of 2000 or hydroxypropylmethyl cellulose, no significant difference was observed as shown in Table 3; this means that the use of water-soluble polymer material does not affect the measured results of the sensitivity test. In Table 3, 0.1 mg of poly(vinyl alcohol) or hydroxylpropylmethyl cellulose was contained in a sheet of disk carrier made of filter paper having a diameter of 6.0 mm and a thickness of 0.7 mm.

TABLE 3

(unit: mm)

| | Antibiotic | | | | | |
|---|---|---|---|---|---|---|
| | Cefotiam hydrochloride 30 μg/disc | | | Cefsulodin sodium 30 μg/disc | | |
| | Polymer material | | | | | |
| Strain | PVA | HPMC | None | PVA | HPMC | None |
| Pseudomonas aeruginosa IFO 3919 | — | — | — | 28 | 28 | 28 |
| Bacillus subtilis ATCC 6633 | 35 | 35 | 35 | 13 | 13 | 13 |
| Serratia marcescens IFO 3736 | 19 | 19 | 19 | 12 | 12 | 12 |
| Serratia marcescens IFO 3759 | 24 | 24 | 24 | 11 | 11 | 11 |
| Staphylococcus aureus IFO 3183 | 29 | 29 | 29 | 23 | 23 | 23 |

(Note)
PVA = Poly(vinyl alcohol) having a degree of polymerization of about 2000 was used as water-soluble polymer material.
HPMC = Hydroxypropylmethyl cellulose was used as water-soluble polymer material.

The present invention is not limited to the measurement of the sensitivity of the bacteria mentioned above. Any other bacteria or other microorganism can be tested with good reliability and reproducibility.

According to this invention, the sensitivity test disks having good stability for a long period of time without adverse effects on the measured results can be obtained by impregnating disk carriers uniformly with a water-soluble polymer material.

As to the test method using the sensitivity test disks, there are generally employed the so-called one-concentration method, two-concentrations method, three-concentrations method, and the like. The concentrations of the antibacterial agents are changed depending on the test methods. The sensitivity test disk according to the present invention can be applied to all the test methods mentioned above irrespective of the concentrations of antibacterial agents without causing any problems.

This invention is illustrated by way of the following Examples.

EXAMPLE 1

In 100 ml of a 0.1 M citrate buffer solution having a pH of 4.0, 0.5 g of poly(vinyl alcohol) having a degree of polymerization of 2000 was dissolved. To the resulting solution, 150 mg of cefotiam hydrochloride was added and dissolved. The resulting solution containing the antibiotic was dropped on circular filter paper previously cut so as to have a diameter of 6.0 mm in an amount of 20 μl using a micropipette. The drug impregnated filter paper was dried under reduced pressure to give sensitivity test disks each containing 30 μg of cefotiam hydrochloride. The thus prepared sensitivity test disks showed retention of potency of above 90% when allowed to stand at 20° C. for 10 days under a humidity of 65%.

When sentivity test disks were prepared according to a conventional method without using a water-soluble polymer material, the retention of potency under the same conditions as mentioned above was only less than 60%.

EXAMPLE 2

The process of Example 1 was repeated except for using cefsulodin sodium in place of cefotiam hydrochloride to give sensitivity test disks each containing 30 μg of cefsulodin sodium. The resulting test disks showed the same good stability as in Example 1.

EXAMPLE 3

In 100 ml of a 0.1 M citrate buffer solution having a pH of 4.0, 0.5 g of hydroxypropyl cellulose was dissolved. To the resulting solution, 150 mg of cefotiam hydrochloride was added and dissolved.

The resulting solution containing the antibiotic was dropped on circular filter paper previously cut so as to have a diameter of 6.0 mm in an amount of 20 μl using a micropipette. The drug impregnated filter paper was dried under reduced pressure to give sensitivity test disks each containing 30 μg of cefotiam hydrochloride. The resulting test disks showed the same good stability as in Example 1.

EXAMPLE 4

The process of Example 3 was repeated except for using cefsulodin sodium in place of cefotiam hydrochloride to give sensitivity test disks each containing 30 μg of cefsulodin sodium. The resulting test disks showed the same good stability as in Example 1.

EXAMPLE 5

In 100 ml of distilled water, 0.5 g of poly(vinyl alcohol) having a degree of polymerization of 2000 was dissolved. To the resulting solution, 150 mg of benzylpenicillin potassium was added and dissolved. The resulting solution containing the antibiotic was dropped on circular filter paper previously cut so as to have a diameter of 6.0 mm in an amount of 20 μl using a micropipette. The drug impregnated filter paper was dried under reduced pressure to give sensitivity test disks each containing 30 μg of benzylpenicillin potassium. The resulting test disks showed the same good stability as in Example 1.

EXAMPLE 6

In 100 ml of distilled water 0.5 g of hydroxypropylmethyl cellulose was dissolved. To the resulting solution, 150 mg of benzylpenicillin potassium was added and dissolved. The resulting solution containing the antibiotic was dropped on circular filter paper previously cut so as to have a diameter of 6.0 mm in an amount of 20 μl using a micropipette. The drug impregnated filter paper was dried under reduced pressure to give sensitivity test disks each containing 30 μg of benzylpenicillin potassium. The resulting test disks showed the same good stability as in Example 1.

EXAMPLE 7

The process of Example 1 was repeated except for using cefmenoxime hydrochloride in place of cefotiam hydrochloride to give sensitivity test disks each containing 30 μg of cefmenoxime hydrochloride. The resulting test disks showed the same good stability as in Example 1.

EXAMPLE 8

In 100 ml of a 0.1 M citrate buffer solution having a pH of 6.0, 0.5 g of poly(vinyl alcohol) having a degree of polymerization of 2000 was dissolved. To the resulting solution, 150 mg of mecillinam was added and dissolved. The resulting solution containing the antibiotic was dropped on circular filter paper previously cut so as to have a diameter of 6.0 mm in an amount of 20 μl using a micropipette. The drug impregnated filter paper was dried under reduced pressure to give sensitivity test disks each containing 30 μg of mecillinam (a metabolic product of pivmecillinam hydrochloride). The resulting test disks showed the same good stability as in Example 1.

EXAMPLE 9

In 5 liters of 0.1M citrate buffer solution having a pH of 4.0, 25 g of poly(vinyl alcohol) having a degree of polymerization of 2000 was dissolved. To the resulting solution, 7.5 g of cefotiam hydrochloride was added and dissolved to give an impregnating solution. A sheet of filter paper having a thickness of 0.7 mm was impregnated with the impregnating solution, dried by an air-blowing drying at room temperature to give antibiotic impregnated filter paper. The resulting antibiotic impregnated filter paper was punched by a punching machine to give disks having a diameter of 6.0 mm and containing cefotiam hydrochloride in an amount of 30 μg.

EXAMPLE 10

The process of Example 9 was repeated except for using 7.5 g of cefsulodin sodium in place of 7.5 g of cefotiam hydrochloride to give sensitivity test disks containing 30 μg of cefsulodin sodium.

EXAMPLE 11

The process of Example 9 was repeated except for using 7.5 g of cefmenoxime hydrochloride in place of 7.5 g of cefotiam hydrochloride to give sensitivity test disks containing 30 μg of cefmenoxime hydrochloride.

EXAMPLE 12

In 1 liter of 0.1M citrate buffer solution having a pH of 6.0, 5 g of poly(vinyl alcohol) having a degree of polymerization of 2000 was dissolved. To the resulting solution, 1.5 g of mecillinam was added and dissolved to give an impregnating solution. A sheet of filter paper having a thickness of 0.7 mm was impregnated with the impregnating solution, dried by an air-blowing drying at room temperature to give antibiotic impregnated filter paper. The resulting antibiotic impregnated filter paper was punched by a punching machine to give disks having a diameter of 6.0 mm and containing mecillinam (a metabolic product of pivmecillinam hydrochloride) in an amount of 30 μg.

Stabilities of the disks obtained in Examples 9 to 11 were as shown in Table 4.

TABLE 4

| Example No. | Antibiotics | Retention of potency of antibiotics (%) | | | | |
|---|---|---|---|---|---|---|
| | | At the time of production | After 1 month | After 3 months | After 6 months | After 12 months |
| 9 | Cefotiam hydrochloride | 100 | 99.7 | 99.0 | 98.7 | 95.4 |
| 10 | Cefsulodin | 100 | 99.3 | 99.0 | 98.0 | 94.8 |

TABLE 4-continued

| Example No. | Antibiotics | Retention of potency of antibiotics (%) | | | | |
|---|---|---|---|---|---|---|
| | | At the time of production | After 1 month | After 3 months | After 6 months | After 12 months |
| 11 | sodium Cefmenoxime hydrochloride | 100 | 99.7 | 98.7 | 97.7 | 94.7 |

(Note) Stored at 25° C. using a desiccant.

What is claimed is:

1. In a sensitivity test disk used for determining the sensitivity of microorganisms to antibacterial agents, said sensitivity test disk being obtained by impregnating a disk carrier with an aqueous solution of antibacterial agent and drying said disk carrier, the improvement wherein a stabilizer consisting essentially of a water-soluble polymer in a concentration of 0.1 to 1.0% by weight of the aqueous solution, having film-forming properties is dissolved in the aqueous solution of antibacterial agent, said polymer, upon drying of the impregnated disk carrier to give a sensitivity test disk, forms a film of which covers the antibacterial agent to protect it from atmospheric moisture.

2. A sensitivity test disk according to claim 1, wherein the water-soluble polymer material is poly(vinyl alcohol) having a degree of polymerization of 500 to 2000.

3. A sensitivity test disk according to claim 1, wherein the water-soluble polymer material is at least one member selected from the group consisting of methyl cellulose, hydroxypropylmethyl cellulose, hydroxypropylethyl cellulose, hydroxypropyl cellulose, and hydroxyethyl cellulose.

4. A sensitivity test disk according to claim 1, wherein the aqueous solution further contains a buffer solution.

5. A sensitivity test disk according to claim 1, wherein the antibacterial agent is a cephem antibiotic.

6. A sensitivity test disk according to claim 1, wherein the antibacterial agent is a penicillin antibiotic.

7. A process for stabilizing a sensitivity test disk used for determining the sensitivity of microorganisms to antibacterial agents which comprises impregnating a disk carrier with an aqueous solution containing an antibacterial agent and further containing as a stabilizer a water-soluble polymer in a concentration of 0.1 to 1.0% by weight of the aqueous solution, having film-forming properties, and drying the impregnated disk carrier, whereby said polymer forms a film which protects the antibacterial agent from atmospheric moisture.

8. A process for stabilizing a sensitivity test disk used for determining the sensitivity of microorganisms to antibacterial agents which comprises impregnating a disk carrier with an aqueous solution containing an antibacterial agent and drying said disk carrier, impregnating the dried disk carrier with an aqueous solution containing as a stabilizer a water-soluble polymer in a concentration of 0.1 to 1.0% by weight of the aqueous solution, having film-forming properties, and drying the impregnated disk carrier, whereby said polymer forms a film which protects the antibacterial agent from atmospheric moisture.

* * * * *

UNITED STATES PATENT AND TRADEMARK OFFICE
CERTIFICATE OF CORRECTION

PATENT NO. : 4,714,675

DATED : Dec. 22, 1987

INVENTOR(S) : Yoshinobu Miyashita et al.

It is certified that error appears in the above-identified patent and that said Letters Patent is hereby corrected as shown below:

On the Title page, Item [73] Assignee should read:

-- Takeda Chemical Industries, Ltd., Osaka, Japan --.

Signed and Sealed this

First Day of November, 1988

Attest:

DONALD J. QUIGG

Attesting Officer

Commissioner of Patents and Trademarks